United States Patent [19]

Rosenberg et al.

[11] Patent Number: 5,679,782
[45] Date of Patent: Oct. 21, 1997

[54] OLIGONUCLEOTIDES ENCLODING PEPTIDE INHIBITORS OF UROKINASE RECEPTOR ACTIVITY

[75] Inventors: Steven Rosenberg; Michael V. Doyle, both of Oakland, Calif.

[73] Assignee: Chiron Corporation

[21] Appl. No.: 438,759

[22] Filed: May 10, 1995

Related U.S. Application Data

[62] Division of Ser. No. 370,567, Jan. 9, 1995, which is a continuation of Ser. No. 61,514, May 28, 1993, abandoned.

[51] Int. Cl.$^6$ ............................ C12N 15/11; C12N 15/12
[52] U.S. Cl. ............................................ 536/23.1; 536/23.5
[58] Field of Search ................................... 536/23.1, 23.5

[56] References Cited

U.S. PATENT DOCUMENTS

| | | | |
|---|---|---|---|
| 5,340,833 | 8/1994 | Bridges | 574/443 |
| 5,416,006 | 5/1995 | Blasi et al. | 435/69.1 |
| 5,519,120 | 5/1996 | Danø et al. | 530/388.8 |

FOREIGN PATENT DOCUMENTS

| | | |
|---|---|---|
| WO92/02553 | 2/1992 | WIPO. |
| WO93/09808 | 5/1993 | WIPO. |

OTHER PUBLICATIONS

Appella et al., *J. Biol. Chem.*, "The Receptor–binding Sequences of Urokinase", (1987) 262(10):4437–4440.

*Primary Examiner*—Stephen Walsh
*Assistant Examiner*—Michael D. Pak
*Attorney, Agent, or Firm*—Grant D. Green; Ling-Fong Chung; Robert P. Blackburn

[57] ABSTRACT

Oligonucleotides encoding effective urokinase-type plasminogen activator receptor antagonists have amino acid sequences selected from the group AEPMPHSLNFSQYLWYT, AEWHPGLSFGSYLWSKT, AEHTYSSLWDTYSPLAF, AESSLWTRYAWPSMPSY, AELDLWMRHYPLSFSNR, AEWSFYNLHLPEPQTIF, AETLFMDLWHDKHILLT, AEPLDLWSLYSLPPLAM, AESLPTLTSILWGKESV, AESQTGTLNTLFWNTLR, AESSLWRIFSPSALMMS, AEPALLNWSFFFNPGLH, AEAWFLSNTMKALSARL, AEPTLWQLYQFPLRLSG, AEISFSELMWLRSTPAF, AEWITSSPPLTQYLWGF, AEMHRSLWEWYVPNQSA, AEIKTDEKMGLWDLYSM, AEILNFPLWHEPLWSTE, AELSEADLWITWFGMGS, AESVQYSKLWKPNTTLA, AEPLSLYQKKTLRHFAN, AELPRTNPVTAVKNPSF, AEQLNRSIPDLQFSMFN, and AESHIKSLLDSSTWFLP, or active analogs or active portions thereof.

1 Claim, No Drawings

OLIGONUCLEOTIDES ENCLODING PEPTIDE INHIBITORS OF UROKINASE RECEPTOR ACTIVITY

RELATED APPLICATIONS

This application is a divisional of U.S. patent application Ser. No. 08/370,567, filed 9 Jan. 1995; which is a continuation of U.S. patent application Ser. No. 08/061,514, filed 28 May 1993, now abandoned.

DESCRIPTION

Technical Field

This invention relates to the fields of cellular biology and protein expression. More particularly, the invention relates to peptide ligands of the urokinase plasminogen activator receptor, and methods for preparing the same.

Background of the Invention

Urokinase-type plasminogen activator (uPA) is a multidomain serine protease, having a catalytic "B" chain (amino acids 144–411), and an amino-terminal fragment ("ATF", aa 1–143) consisting of a growth factor-like domain (4–43) and a kringle (aa 47–135). The uPA kringle appears to bind heparin, but not fibrin, lysine, or aminohexanoic acid. The growth factor-like domain bears some similarity to the structure of epidermal growth factor (EGF), and is thus also referred to as an "EGF-like" domain. The single chain pro-uPA is activated by plasmin, cleaving the chain into the two chain active form, which is linked together by a disulfide bond.

uPA binds to its specific cell surface receptor (uPAR). The binding interaction is apparently mediated by the EGF-like domain (S. A. Rabbani et al.; *J Biol Chem* (1992) 267:14151–56). Cleavage of pro-uPA into active uPA is accelerated when pro-uPA and plasminogen are receptor-bound. Thus, plasmin activates pro-uPA, which in turn activates more plasmin by cleaving plasminogen. This positive feedback cycle is apparently limited to the receptor-based proteolysis on the cell surface, since a large excess of protease inhibitors is found in plasma, including $\alpha_2$ antiplasmin, PAI-1 and PAI-2.

Plasmin can activate or degrade extracellular proteins such as fibrinogen, fibronectin, and zymogens. Plasminogen activators thus can regulate extracellular proteolysis, fibrin clot lysis, tissue remodeling, developmental cell migration, inflammation, and metastasis. Accordingly, there is great interest in developing uPA inhibitors and uPA receptor antagonists. E. Appella et al., *J Biol Chem* (1987) 262:4437–40, determined that receptor binding activity is localized in the EGF-like domain, and that residues 12–32 appear to be critical for binding. The critical domain alone ($uPA_{12-32}$) bound uPAR with an affinity of 40 nM (about 100 fold less than intact ATF).

S. A. Rabbani et al., supra, disclosed that the EGF-like domain is fucosylated at $Thr_{18}$, and reported that fucosylated EGF-like domain ($uPA_{4-43}$, produced by cleavage from pro-uPA) was mitogenic for an osteosarcoma cell line, SaOS-2. In contrast, non-fucosylated EGF-like domain bound uPAR with an affinity equal to the fucosylated EGF-like domain, but exhibited no mitogenic activity. Non-fucosylated EGF-like domain competed for binding to uPAR with fucosylated EGF-like domain, and reduced the mitogenic activity observed. Neither fucosylated nor non-fucosylated EGF-like domain was mitogenic in U937 fibroblast cells.

Previously, it was suggested that an "epitope library" might be made by cloning synthetic DNA that encodes random peptides into filamentous phage vectors (Parmley and Smith, *Gene* (1988) 73:305). It was proposed that the synthetic DNA be cloned into the coat protein gene III because of the likelihood of the encoded peptide becoming part of pIII without significantly interfering with pIII's function. It is known that the amino terminal half of pIII binds to the F pilus during infection of the phage into *E. coli*. It was suggested that such phage that carry and express random peptides on their cell surface as part of pIII may provide a way of identifying the epitopes recognized by antibodies, particularly using antibody to affect the purification of phage from the library. Devlin, PCT WO91/18980 (incorporated herein by reference) described a method for producing a library consisting of random peptide sequences presented on filamentous phage. The library can be used for many purposes, including identifying and selecting peptides that have a particular bioactivity. An example of a ligand binding molecule would be a soluble or insoluble cellular receptor (i.e., a membrane bound receptor), but would extend to virtually any molecule, including enzymes; that have the sought after binding activity. Description of a similar library is found in Dower et al., WO91/19818. The present invention provides a method for screening such libraries (and other libraries of peptides) to determine bioactive peptides or compounds. Kang et al., WO92/18619 disclosed a phage library prepared by inserting into the pVIII gene.

DISCLOSURE OF THE INVENTION

One aspect of the invention is the set of polypeptides disclosed herein, and analogs thereof, which bind to the urokinase plasminogen activator receptor and inhibit the receptor binding activity of urokinase-type plasminogen activator.

Another aspect of the invention is a method for treating a urokinase-modulated disorder, such as cancer and metastasis, by administering an effective amount of a peptide of the invention or an analog thereof.

Another aspect of the invention is a composition suitable for treating a urokinase-modulated disorder, comprising an effective amount of a peptide of the invention or an analog thereof in combination with a pharmaceutically acceptable excipient.

MODES OF CARRYING OUT THE INVENTION

A. DEFINITIONS

The term "huPA" refers specifically to human urokinase-type plasminogen activator. The "EGF-like domain" is that portion of the huPA molecule responsible for mediating huPA binding to its receptor (uPAR). The EGF-like domain, sometimes called the growth factor-like domain ("GFD"), is located within the first 48 residues of huPA. The critical residues (essential for binding activity) have been localized to positions 12–32, although a peptide containing only those residues does not exhibit a binding affinity high enough to serve as a useful receptor antagonist.

"Peptides of the invention" and "huPAR antagonist peptides" have one of the following sequences:

AEPMPHSLNFSQYLWYT (SEQ ID NO:1),
AEWHPGLSFGSYLWSKT (SEQ ID NO:2),
AEHTYSSLWDTYSPLAF (SEQ ID NO:3),
AESSLWTRYAWPSMPSY (SEQ ID NO:4),

AELDLWMRHYPLSFSNR (SEQ ID NO:5),
AEWSFYNLHLPEPQTIF (SEQ ID NO:6),
AETLFMDLWHDKHILLT (SEQ ID NO:7),
AEPLDLWSLYSLPPLAM (SEQ ID NO:8),
AESLPTLTSILWGKESV (SEQ ID NO:9),
AESQTGTLNTLFWNTLR (SEQ ID NO:10),
AESSLWRIFSPSALMMS (SEQ ID NO:11),
AEPALLNWSFFFNPGLH (SEQ ID NO:12),
AEAWFLSNTMKALSARL (SEQ ID NO:13),
AEPTLWQLYQFPLRLSG (SEQ ID NO:14),
AEISFSELMWLRSTPAF (SEQ ID NO:15),
AEWITSSPPLTQYLWGF (SEQ ID NO:16),
AEMHRSLWEWYVPNQSA (SEQ ID NO:17),
AEIKTDEKMGLWDLYSM (SEQ ID NO:18),
AEILNFPLWHEPLWSTE (SEQ ID NO:19),
AELSEADLWITWFGMGS (SEQ ID NO:20),
AESVQYSKLWKPNTTLA (SEQ ID NO:21),
AEPLSLYQKKTLRHFAN (SEQ ID NO:22),
AELPRTNPVTAVKNPSF (SEQ ID NO:23),
AEQLNRSIPDLQFSMFN (SEQ ID NO:24),
AESHIKSLLDSSTWFLP (SEQ ID NO:25).

The term "active analog" refers to a polypeptide differing from the sequence of one of the peptides of the invention, or an active portion thereof by 1–7 amino acids, but which still exhibits a $K_d < 5$ μM with huPAR. The differences are preferably conservative amino acid substitutions, in which an amino acid is replaced with another naturally-occurring amino acid of similar character. For example, the following substitutions are considered "conservative": Gly↔Ala; Val↔Ile↔Leu; Asp↔Glu; Lys↔Arg; Asn↔Gln; and Phe↔Trp↔Tyr. Nonconservative changes are generally substitutions of one of the above amino acids with an amino acid from a different group (e.g., substituting Asn for Glu), or substituting Cys, Met, His, or Pro for any of the above amino acids. An "active portion" of a peptide of the invention is a peptide which exhibits huPA receptor binding activity, and which comprises a sequence identical to at least six consecutive amino acids derived from one of the peptides of the invention, preferably at least eight amino acids, most preferably at least nine amino acids, but less than seventeen amino acids. The huPAR antagonist peptides of the invention should be substantially free of peptides derived from other portions of the huPA protein. For example, a huPAR antagonist composition should contain less than 20 wt % huPA B domain (dry weight, absent excipients), preferably less than 10 wt % huPA-B, more preferably less than 5 wt % huPA-B, most preferably no detectable amount.

The term "fusion protein" refers to a protein of the form:

$$X_1\text{-(peptide)}_n\text{-}X_2$$

in which at least one of $X_1$ and $X_2$ is a protein or polypeptide, (peptide) is a peptide of the invention or an active analog or active portion thereof, and n is an integer from 1 to 100. $X_1$ and $X_2$ may be the same or different, and may be portions of the same protein (e.g., the peptide may be inserted at an internal position within the primary sequence of another protein). $X_1$ and $X_2$ may be selected to improve expression of the peptide/fusion protein, to enhance purification, and/or to provide a biological activity. The peptides of the invention may be the same or different, and may be separated by peptide spacers (e.g., if it is desired to prepare a fusion protein capable of crosslinking huPAR on the cell surface). Alternatively, the peptides may be separated by proteolytic cleavage sites, to facilitate cleavage of the fusion protein into individual active peptides.

"Active peptoid analog" refers to an analog of one of the peptides of the invention wherein one or more of the amino acids is replaced by a non-conventional amino acid. Peptoids are described in more detail in Bartlett et al., PCT WO91/19735, incorporated herein by reference. In general, conservative replacements are preferred. Conservative replacements substitute the original amino acid with a nonconventional amino acid that resembles the original in one or more of its characteristic properties (e.g., charge, hydrophobicity, stearic bulk). For example, one may replace Val with Nval. The term "conventional amino acid" refers to the amino acids alanine (A), cysteine (C), aspartic acid (D), glutamic acid (E), phenylalanine (F), glycine (G), histidine (H), isoleucine (I), lysine (K), leucine (L), methionine (M), asparagine (N), proline (P), glutamine (Q), arginine (R), serine (S), threonine (T), valine (V), tryptophan (W), and tyrosine (Y). The term "nonconventional amino acid" refers to amino acids other than conventional amino acids. Presently preferred nonconventional amino acids are:

| | |
|---|---|
| Nle = L-norleucine; | Aabu = α-aminobutyric acid; |
| Hphe = L-homophenylalanine; | Nva = L-norvaline; |
| Gabu = γ-aminobutyric acid; | Dala = D-alanine; |
| Dcys = D-cysteine; | Dasp = D-aspartic acid; |
| Dglu = D-glutamic acid; | Dphe = D-phenylalanine; |
| Dhis = D-histidine; | Dile = D-isoleucine; |
| Dlys = D-lysine; | Dleu = D-leucine; |
| Dmet = D-methionine; | Dasn = D-asparagine; |
| Dpro = D-proline; | Dgln = D-glutamine; |
| Darg = D-arginine; | Dser = D-serine; |
| Dthr = D-threonine; | Dval = D-valine; |
| Dtrp = D-tryptophan; | Dtyr = D-tyrosine; |
| Dorn = D-ornithine; | Aib = aminoisobutyric acid; |
| Etg = L-ethylglycine; | Tbug = L-t-butylglycine; |
| Pen = penicillamine; | Anap = α-naphthylalanine; |
| Chexa = cyclohexylalanine; | Cpen = cyclopentylalanine; |
| Cpro = aminocyclopropane carboxylate; | Norb = aminonorbornylcarboxylate; |
| Mala = L-α-methylalanine; | Mcys = L-α-methylcysteine; |
| Masp = L-α-methylaspartic acid; | Mglu = L-α-methylglutamic acid; |
| Mphe = L-α-methylphenylalanine; | Mhis = L-α-methylhistidine; |
| Mile = L-α-methylisoleucine; | Mlys = L-α-methyllysine; |
| Mleu = L-α-methylleucine; | Mmet = L-α-methylmethionine; |
| Masn = L-α-methylasparagine; | Mpro = L-α-methylproline; |
| Mgln = L-α-methylglutamine; | Marg = L-α-methylarginine; |

-continued

| | |
|---|---|
| Mser = L-α-methylserine; | Mthr = L-α-methylthreonine; |
| Mval = L-α-methylvaline; | Mtrp = L-α-methyltryptophan; |
| Mtyr = L-α-methyltyrosine; | Morn = L-α-methylornithine; |
| Mnle = L-α-methylnorleucine; | Maabu = α-amino-α-methylbutylic acid; |
| Mnva = L-α-methylnorvaline; | Mhphe = L-α-methylhomophenylalanine; |
| Metg = L-α-methylethylglycine; | Mgabu = α-methyl-γ-aminobutyric acid; |
| Maib = α-methylaminoisobutyric acid; | Mtbug = L-α-methyl-t-butylglycine; |
| Mpen = α-methylpenicillamine; | Manap = α-methyl-α-naphthylalanine. |
| Mchexa = α-methylcyclohexylalanine; | Mcpen = α-methylcyclopentylalanine; |
| Dmala = D-α-methylalanine; | Dmorn = D-α-methylornithine; |
| Dmcys = D-α-methylcysteine; | Dmasp = D-α-methylaspartic acid; |
| Dmglu = D-α-methylglutamic acid; | Dmphe = D-α-methylphenylalanine; |
| Dmhis = D-α-methylhistidine; | Dmile = D-α-methylisoleucine; |
| Dmlys = D-α-methyllysine; | Dmleu = D-α-methylleucine; |
| Dmmet = D-α-methylmethionine; | Dmasn = D-α-methylasparagine; |
| Dmpro = D-α-methylproline; | Dmgln = D-α-methylglutamine; |
| Dmarg = D-α-methylarginine; | Dmser = D-α-methylserine; |
| Dmthr = D-α-methylthreonine; | Dmval = D-α-methylvaline; |
| Dmtrp = D-α-methyltryptophan; | Dmtyr = D-α-methyltyrosine; |
| Nmala = L-N-methylalanine; | Nmcys = L-N-methylcysteine; |
| Nmasp = L-N-methylaspartic acid; | Nmglu = L-N-methylglutamic acid; |
| Nmphe = L-N-methylphenylalanine; | Nmhis = L-N-methylhistidine; |
| Nmile = i-N-methylisoleucine; | Nmlys = L-N-methyllysine; |
| Nmleu = L-N-methylleucine; | Nmmet = L-N-methylmethionine; |
| Nmasn = L-N-methylasparagine; | Nmchexa = N-methylcyclohexylalanine; |
| Nmgln = L-N-methylglutamine; | Nmarg = L-N-methylarginine; |
| Nmser = L-N-methylserine; | Nmthr = L-N-methylthreonine; |
| Nmval = L-N-methylvaline; | Nmtrp = L-N-methyltryptophan; |
| Nmtyr = L-N-methyltyrosine; | Nmorn = L-N-methylornithine; |
| Nmnle = L-N-methylnorleucine; | Nmaabu = N-amino-α-methylbutyric acid; |
| Nmnva = L-N-methylnorvaline; | Nmhphe = L-N-methylhomophenylalanine; |
| Nmetg = L-N-methylethylglycine; | Nmgabu = N-methyl-γ-aminobutyric acid; |
| Nmcpen = N-methylcyclopentylalanine: | Nmtbug = L-N-methyl-t-butylglycine; |
| Nmpen = N-methylpenicillamine; | Nmanap = N-methyl-α-naphthylalanine; |
| Nmaib = N-methylaminoisobutyric acid; | Dnmorn = D-N-methylornithine; |
| Dnmala = D-N-methylalanine; | Dnmasp = D-N-methylaspartic acid; |
| Dnmcys = D-N-methylcysteine; | Dnmphe = D-N-methylphenylalanine; |
| Dnmglu = D-N-methylglutamic acid; | Dnmile = D-N-methylisoleucine; |
| Dnmhis = D-N-methylhistidine; | Dnmleu = D-N-methylleucine; |
| Dnmlys = D-N-methyllysine; | Dnmasn = D-N-methylasparagine; |
| Dnmmet = D-N-methylmethionine; | Dnmgln = D-N-methylglutamine; |
| Dnmpro = D-N-methylproline; | Dnmser = D-N-methylserine; |
| Dnmarg = D-N-methylarginine; | Dnmval = D-N-methylvaline; |
| Dnmthr = D-N-methylthreonine; | Dnmtyr = D-N-methyltyrosine; |
| Dnmtrp = D-N-methyltryptophan; | Nasp = N-(carboxymethyl)glycine; |
| Nala = N-methylglycine (sarcosine); | Nphe = N-benzylglycine; |
| Nglu = N-(2-carboxyethyl)glycine; | Nile = N-(1-methylpropyl)glycine, |
| Nhhis = N-(imidazolylethyl)glycine; | Nleu = N-(2-methylpropyl)glycine; |
| Nlys = N-(4-aminobutyl)glycine; | Nhser = N-(hydroxyethyl)glycine; |
| Nmet = N-(2-methylthioethyl)glycine; | Ngln = N-(2-carbamylethyl)glycine; |
| Nasn = N-(carbamylmethyl)glycine; | Narg = N-(3-guanidinopropyl)glycine; |
| Nval = N-(1-methylethyl)glycine; | Nhtyr = N-(p-hydroxyphenethyl)glycine; |
| Nhtrp = N-(3-indolylethyl)glycine; | Ncys = N-(thiomethyl)glycine; and |
| Nthr = N-(1-hydroxyethyl)glycine; | Ncpro = N-cyclopropylglycine; |
| Norn = N-(3-aminopropyl)glycine; | Nchex = N-cyclohexylglycine; |
| Ncbut = N-cyclobutyglycine; | Nooct = N-cyclooctylglycine; |
| Nchep = N-cycloheptylglycine; | Ncund = N-cycloundecylglycine; |
| Ncdec = N-cyclodecylglycine; | Nbhm = N-(2,2-diphenylethyl)glycine; |
| Nedod = N-cyclododecylglycine; | |

Nbhe N-(3,3-diphenylpropyl)glycine;
Nnbhm N-(N-(2,2-diphenylethyl)carbamylmethyl)glycine;
Nnbhe N-(N-(3,3-diphenylpropyl)carbamylmethyl)glycine;
Nbmc 1-carboxy-1-(2,2-diphenylethylamino)cyclopropane; and
Naeg N-(2-aminoethyl)glycine.

The term "expression vector" refers to an oligonucleotide which encodes the huPAR antagonist polypeptide of the invention and provides the sequences necessary for its expression in the selected host cell. Expression vectors will generally include a transcriptional promoter and terminator, or will provide for incorporation adjacent to an endogenous promoter. Expression vectors will usually be plasmids, further comprising an origin of replication and one or more selectable markers. However, expression vectors may alternatively be viral recombinants designed to infect the host, or integrating vectors designed to integrate at a preferred site within the host's genome. Expression vectors may further comprise an oligonucleotide encoding a signal leader polypeptide. When "operatively connected", the huPAR antagonist is expressed downstream and in frame with the signal leader, which then provides for secretion of the huPAR antagonist polypeptide by the host to the extracellular medium. The presently preferred signal leader is the *Saccharomyces cerevisiae* α-factor leader (particularly when modified to delete extraneous Glu-Ala sequences).

The term "transcriptional promoter" refers to an oligonucleotide sequence which provides for regulation of the DNA→mRNA transcription process, typically based on temperature, or the presence or absence of metabolites, inhibitors, or inducers. Transcriptional promoters may be regulated (inducible/repressible) or constitutive. Yeast glycolytic enzyme promoters are capable of driving the transcription and expression of heterologous proteins to high levels, and are particularly preferred. The presently preferred promoter is the hybrid ADH2/GAP promoter described in Tekamp-Olson et al., U.S. Pat. No. 4,876,197 (incorporated herein by reference), comprising the S. cerevisiae glyceraldehyde-3-phosphate dehydrogenase promoter in combination with the S. cerevisiae alcohol dehydrogenase II upstream activation site.

The term "host" refers to a yeast cell suitable for expressing heterologous polypeptides. There are a variety of suitable genera, such as Saccharomyces, Schizosaccharomyces, Kluveromyces, Pichia, Hansenula, and the like. Presently preferred are yeast of the Saccharomyces genus, particularly Saccharomyces cerevisiae.

The term "huPA-mediated disorder" refers to a disease state or malady which is caused or exacerbated by a biological activity of huPA. The primary biological activity exhibited is plasminogen activation. Disorders mediated by plasminogen activation include, without limitation, inappropriate angiogenesis (e.g., diabetic retinopathy, corneal angiogenesis, Kaposi's sarcoma, and the like), metastasis and invasion by tumor cells, and chronic inflammation (e.g., rheumatoid arthritis, emphysema, and the like). Fucosylated ATF or EGF-like domain are also mitogenic for tumor cells, which sometimes self-activate in an autocrine mechanism. Accordingly, the huPAR antagonist of the invention is effective in inhibiting the proliferation of huPA-activated tumor cells.

The term "effective amount" refers to an amount of huPAR antagonist polypeptide sufficient to exhibit a detectable therapeutic effect. The therapeutic effect may include, for example, without limitation, inhibiting the growth of undesired tissue or malignant cells, inhibiting inappropriate angiogenesis, limiting tissue damage caused by chronic inflammation, and the like. The precise effective amount for a subject will depend upon the subject's size and health, the nature and severity of the condition to be treated, and the like. Thus, it is not possible to specify an exact effective amount in advance. However, the effective amount for a given situation can be determined by routine experimentation based on the information provided herein.

The term "pharmaceutically acceptable" refers to compounds and compositions which may be administered to mammals without undue toxicity. Exemplary pharmaceutically acceptable salts include mineral acid salts such as hydrochlorides, hydrobromides, phosphates, sulfates, and the like; and the salts of organic acids such as acetates, propionates, malonates, benzoates, and the like.

B. GENERAL METHOD

The peptides of the invention may be synthesized by standard chemical methods, such as solid phase peptide synthesis. Alternatively, if desired, the peptides may be expressed in an appropriate host. Peptides prepared as part of a fusion protein are preferably expressed in a host cell. Presently preferred hosts are yeasts, particularly Saccharomyces, Schizosaccharomyces, Kluveromyces, Pichia, Hansenula, and the like, especially S. cerevisiae. Strains MB2-1 and AB110 are presently preferred, as are strains JSC302 and JSC308 (for fusion protein constructs).

The expression vector is constructed according to known methods, and typically comprises a plasmid functional in the selected host. The oligonucleotide encoding the peptide will generally be synthesized chemically, or cloned from a suitable source (e.g., from a bacteriophage library). Stable plasmids generally require an origin of replication (such as the yeast 2μ ori), and one or more selectable markers (such as antibiotic resistance) which can be used to screen for transformants and force retention of the plasmid. The vector should provide a promoter which is functional in the selected host cell, preferably a promoter derived from yeast glycolytic enzyme promoters such as GAPDH, GAL, and ADH2. These promoters are highly efficient, and can be used to drive expression of heterologous proteins up to about 10% of the host cell weight. The presently preferred promoter is a hybrid ADH2/GAP promoter comprising the S. cerevisiae glyceraldehyde-3-phosphate dehydrogenase promoter in combination with the S. cerevisiae alcohol dehydrogenase II upstream activation site.

The expression vector should ideally provide a signal leader sequence between the promoter and the huPAR antagonist polypeptide sequence. The signal leader sequence provides for translocation of the huPAR antagonist polypeptide through the endoplasmic reticulum and export from the cell into the extracellular medium, where it may be easily harvested. There are a number of signal leader sequences known that are functional in yeast. Presently preferred are the yeast α-factor leader (see U.S. Pat. No. 4,751,180, incorporated herein by reference).

Alternatively, the vector may provide for integration into the host genome, as is described by Shuster, PCT WO92/01800, incorporated herein by reference.

Transformations into yeast can be carried out according to the method of A. Hinnen et al., Proc Natl Acad Sci USA (1978) 75:1929–33, or H. Ito et al., J Bacteriol. (1983) 153:163–68. After DNA is taken up by the host cell, the vector integrates into the yeast genome at one or more sites homologous to its targeting sequence. It is presently preferred to linearize the vector by cleaving it within the targeting sequence using a restriction endonuclease, as this procedure increases the efficiency of integration.

Following successful transformations, the number of integrated sequences may be increased by classical genetic techniques. As the individual cell clones can carry integrated vectors at different locations, a genetic cross between two appropriate strains followed by sporulation and recovery of segregants can result in a new yeast strain having the integrated sequences of both original parent strains. Continued cycles of this method with other integratively transformed strains can be used to further increase the copies of integrated plasmids in a yeast host strain. One may also amplify the integrated sequences by standard techniques, for example by treating the cells with increasing concentrations of copper ions (where a gene for copper resistance has been included in the integrating vector).

Correct ligations for plasmid construction may be confirmed by first transforming E. coli strain MM294 obtained from E. coli Genetic Stock Center, CGSC #6135, or other suitable host with the ligation mixture. Successful transformants are selected by ampicillin, tetracycline or other antibiotic resistance or using other markers depending on the plasmid construction, as is understood in the art. Plasmids from the transformants are then prepared according to the method of D. B. Clewell et al., Proc Natl Acad Sci USA (1969) 62:1159, optionally following chloramphenicol amplification (D. B. Clewell, J Bacteriol (1972) 110:667). Isolated DNA is analyzed by restriction mapping and/or sequenced by the dideoxy method of F. Sanger et al., Proc Natl Acad Sci USA (1977) 74:5463 as further described by Messing et al., Nucl Acids Res (1981) 9:309, or by the method of Maxam and Gilbert, Meth Enzymol (1980) 65:499.

Fusion proteins may be prepared by the methods described above. One may improve expression of peptides by expressing them as fusion proteins with a well-expressed protein leader or fusion partner. For example, Cu/Zn superoxide dismutase (SOD) is highly-expressed in yeast when used as a fusion protein leader. See Cousens et al., U.S. Pat. No. 4,751,180, incorporated herein by reference in full. Additionally, one may include secretion leaders, such as the yeast α-factor leader, to direct secretion of the fusion protein to the extracellular medium. One may also employ fusion partners which will impart a biological activity to the fusion protein. For example, one may use a cytotoxic protein in order to kill cells bearing huPAR.

huPAR antagonist polypeptides, active portions, active analogs, active peptoid analogs, and fusion proteins (collectively "antagonists") may be assayed for activity by methods known in the art. For example, active portions, active analogs, and active peptoid analogs may be screened conveniently and efficiently by following the method of H. M. Geysen et al., U.S. Pat. No. 4,708,871. Geysen described a method for synthesizing a set of overlapping oligopeptides derived from any selected protein (e.g., $aa_1$-$aa_7$, $aa_2$-$aa_8$, $aa_3$-$aa_9$, etc.) bound to a solid phase array of pins, with a unique oligopeptide on each pin. The pins are arranged to match the format of a 96-well microtiter plate, permitting one to assay all pins simultaneously, e.g., for binding to a labeled ligand. Using this method, one may readily determine the binding affinity for the ligand for every possible subset of consecutive conventional and/or nonconventional amino acids presented in any selected antagonist. One may assay competition of the antagonist against native huPA for cell surface receptor binding. Competition for the receptor correlates with inhibition of huPA biological activity. One may assay huPAR antagonists for anti-mitogenic activity on appropriate tumor cell lines, such as the osteosarcoma cell line SaOS-2 described in the art. Inhibition of mitogenic activity may be determined by comparing the uptake of $^3$H-T in osteosarcoma cells treated with the antagonist against controls. One may also assay huPAR antagonists for anti-invasive activity on appropriate tumor cell lines, such as HOC-1 and HCT116 (W. Schlechte et al., *Cancer Comm* (1990) 2:173–79; H. Kobayashi et al., *Brit J Cancer* (1993) 67:537–44).

huPAR antagonists are administered orally, topically, or by parenteral means, including subcutaneous and intramuscular injection, implantation of sustained release depots, intravenous injection, intranasal administration, and the like. When used to treat tumors, it may be advantageous to apply the huPAR antagonist peptide directly to the site, e.g., during surgery to remove the bulk of the tumor. Accordingly, huPAR antagonists may be administered as a pharmaceutical composition comprising a huPAR antagonist in combination with a pharmaceutically acceptable excipient. Such compositions may be aqueous solutions, emulsions, creams, ointments, suspensions, gels, liposomal suspensions, and the like. Suitable excipients include water, saline, Ringer's solution, dextrose solution, and solutions of ethanol, glucose, sucrose, dextran, mannose, mannitol, sorbitol, polyethylene glycol (PEG), phosphate, acetate, gelatin, collagen, Carbopol®, vegetable oils, and the like. One may additionally include suitable preservatives, stabilizers, antioxidants, antimicrobials, and buffering agents, for example, BHA, BHT, citric acid, ascorbic acid, tetracycline, and the like. Cream or ointment bases useful in formulation include lanolin, Silvadene® (Marion), Aquaphor® (Duke Laboratories), and the like. Other topical formulations include aerosols, bandages, and other wound dressings.

Alternatively, one may incorporate or encapsulate the huPAR antagonist in a suitable polymer matrix or membrane, thus providing a sustained-release delivery device suitable for implantation near the site to be treated locally. Other devices include indwelling catheters and devices such as the Alzet® minipump. Ophthalmic preparations may be formulated using commercially available vehicles such as Sorbi-care® (Allergan), Neodecadron® (Merck, Sharp & Dohme), Lacrilube®, and the like, or may employ topical preparations such as that described in U.S. Pat. No. 5,124,155, incorporated herein by reference. Further, one may provide a huPAR antagonist in solid form, especially as a lyophilized powder. Lyophilized formulations typically contain stabilizing and bulking agents, for example human serum albumin, sucrose, mannitol, and the like. A thorough discussion of pharmaceutically acceptable excipients is available in *Remington's Pharmaceutical Sciences* (Mack Pub. Co.).

The amount of huPAR antagonist required to treat any particular disorder will of course vary depending upon the nature and severity of the disorder, the age and condition of the subject, and other factors readily determined by one of ordinary skill in the art. The appropriate dosage may be determined by one of ordinary skill by following the methods set forth below in the examples. As a general guide, about 0.10 mg/Kg to about 500 mg/Kg huPAR antagonist administered i.v. or subcutaneously is effective for inhibiting tissue damage due to chronic inflammation. For treating corneal angiogenesis, huPAR antagonist may be administered locally in a gel or matrix at a concentration of about 0.01 mg/Kg to about 50 mg/Kg.

C. EXAMPLES

The examples presented below are provided as a further guide to the practitioner of ordinary skill in the art, and are not to be construed as limiting the invention in any way.

Example 1

(Oligonucleotides Encoding Random Peptides)

An oligonucleotide having the following structure was synthesized, and purified using methods known in the art, as described in Devlin, WO91/18980:

5' CTTTCTATTCTCACTCCGCTGAA(NNS)$_{15}$CCGCCTCCACCTCCACC 3' (SEQ ID NO:26);

5'GGCCGGTGGAGGTGGAGGCGG(NNN)$_{15}$TTCAGCGGAGTGAGAATAGAAAGGTAC 3' (SEQ ID NO:27).

During the synthesis of (NNS)$_{15}$, a mixture consisting of equal amounts of the deoxynucleotides A, C and T, and about 30% more G was used for N, and an equal mixture of C and G for S. Deoxyinosine (i) was used because of its capacity to base pair with each of the four bases (A, G, C, and T) (J. F. Reidhaar-Olson et al., *Science*, (1988) 24:53). Alternatively, other base analogs may be used as described by J. Habener et at., *Proc Natl Acad Sci USA* (1988) 85:1735.

Immediately preceding the nucleotide sequence that encodes the random peptide sequence is a nucleotide sequence that encodes alanine and glutamic acid residues. These amino acids were included because they correspond to the first two amino terminal residues of the wild type mature gene III protein of M13, and thus may facilitate producing the fusion protein produced as described below.

Immediately following the random peptide sequence is a nucleotide sequence that encodes 6 proline residues. Thus, the oligonucleotide encodes the following amino acid sequence:

H₂N-Ala-Glu-Xaa₁₅-Pro₆ (SEQ ID NO:28)

Xaa denotes amino acids encoded by the random DNA sequence. As described below, the oligonucleotides were cloned into a derivative of M13 to produce a mature fusion protein having the above amino acid sequence, and following the proline residues, the entire wild type mature gene III.

Example 2

(Construction of the Plasmid M13LP67)

The plasmid M13LP67 was used to express the random peptide/gene III fusion protein construct. M13LP67 was derived from M13 mp19 as shown in FIGS. 1 and 2.

Briefly, M13mp19 was altered in two ways. The first alteration consisted of inserting the marker gene, β-lactamase, into the polylinker region of the virion. This consisted of obtaining the gene by PCR amplification from the plasmid pAc5. The oligonucleotide primers that were annealed to the pAc5 template have the following sequence:

5' GCTGCCCGAGAGATCTGTATATATGAG-TAAACTTGG 3' (SEQ ID NO:29)

5' GCAGGCTCGGGAATTCGGGAAATGT-GCGCGGAACCC 3' (SEQ ID NO:30)

Amplified copies of the β-lactamase gene were digested with the restriction enzymes BglII and EcoRI, and the replicative form of the modified M13mp19 was digested with Bam HI and EcoRI. The desired fragments were purified by gel electrophoresis, ligated, and transformed into E. coli strain DH5 alpha (BRL). E. coli transformed with phage that carried the insert were selected on ampicillin plates. The phage so produced were termed JD32.

The plasmid form of the phage, pJD32 (M13mp19Amp¹), was mutagenized so that two restriction sites, EagI and KpnI, were introduced into gene III without altering the amino acids encoded in this region. The restriction sites were introduced using standard PCR in vitro mutagenesis techniques as described by M. Innis et al. in "PCR Protocols—A Guide to Methods and Applications" (1990), Academic Press, Inc.

The KpnI site was constructed by converting the sequence, TGTTCC, at position 1611 to GGTACC. The two oligonucleotides used to effect the mutagenesis have the following sequence:

LP159: AAACTTCCTCATGAAAAAGTC (SEQ ID NO:31)

LP162: AGAATAGAAAGGTACCACTAAAGGA (SEQ ID NO:32).

To construct the EagI restriction site, the sequence at position 1631 of pJD32, CCGCTG, was changed to CGGCCG using the following two oligonucleotides:

LP160: TTTAGTGGTACCTTTCTATTCTCACTCG-GCCGAAACTGT (SEQ ID NO:33)

LP161: AAAGCGCAGTCTCTGAATTTACCG (SEQ ID NO:34)

More specifically, the PCR products obtained using the primers LP159, LP162 and LP160 and LP161 were digested with BspHI and KpnI, and KpnI and AlwNI, respectively. These were ligated with T4 ligase to M13mp19 previously cut with BspHI and AlwNI to yield M13mpLP66. This vector contains the desired EagI and KpnI restriction sites, but lacks the ampicillin resistance gene, β-lactamase. Thus, the vector M13mpLP67, which contains the EagI and KpnI restriction sites and β-lactamase was produced by removing the β-lactamase sequences from pJD32 by digesting the vector with XbaI and EcoRI. The β-lactamase gene was then inserted into the polylinker region of M13mpLP66 which was previously digested with XbaI and EcoRI. Subsequent ligation with T4 ligase produced M13mpLP67, which was used to generate the random peptide library. FIGS. 1 and 2 schematically set forth the construction of M13mpLP67.

Example 3

(Production of Phage Encoding Random Peptides)

To produce phage having DNA sequences that encode random peptide sequences, M13LP67 was digested with EagI and KpnI, and ligated to the oligonucleotides produced as described in Example 1 above. The ligation mixture consisted of digested M13LP67 DNA at 45 ng/μL, a 5-fold molar excess of oligonucleotides, 3.6 U/μL of T4 ligase (New England Biolabs), 25 mM Tris, pH 7.8, 10 mM MgCl₂, 2 mM DTT, 0.4 mM ATP, and 0.1 mg/mL BSA. Prior to being added to the ligation mixture, the individual oligonucleotides were combined and heated to 95° C. for 5 minutes, and subsequently cooled to room temperature in 15 μL aliquots. Next, the ligation mixture was incubated for 4 hours at room temperature and subsequently overnight at 15° C. This mixture was then electroporated into E. coli as described below.

M13LP67 DNA was electroporated into H249 cells prepared essentially as described by W. Dower et al., Nuc Acids Res (1988) 16:6127. H249 cells are a recA⁻, sup°, F' kan^R derivative of MM294. Briefly, 4×10⁹ H249 cells and 1 μg of M13LP67 DNA were combined in 85 μL of a low conductivity solution consisting of 1 mM HEPES. The cell/M13LP67DNA mixture was positioned in a chilled 0.56 mm gap electrode of a BTX electroporation device (BTX Corp.) and subjected to a 5 millisecond pulse of 560 volts.

Immediately following electroporation, the cells were removed from the electrode assembly, mixed with fresh H249 lawn cells, and plated at a density of about 2×10⁵ plaques per 400 cm² plate. The next day phage from each plate were eluted with 30 mL of fresh media, PEG precipitated, resuspended in 20% glycerol, and stored frozen at −70° C. About 2.8×10⁷ plaques were harvested and several hundred analyzed to determine the approximate number that harbor random peptide sequences. Using the polymerase chain reaction to amplify DNA in the region that encodes the random peptide sequence, it was determined that about 50–90% of the phage contained a 69 base pair insert at the 5' end of gene III. This confirmed the presence of the oligonucleotides that encode the random peptides sequences. The PCR reaction was conducted using standard techniques and with the following oligonucleotides:

5' TCGAAAGCAAGCTGATAAACCG 3' (SEQ ID NO:35)

5' ACAGACAGCCCTCATAGTTAGCG 3' (SEQ ID NO:36)

The reaction was run for 40 cycles, after which the products were resolved by electrophoresis in a 2% agarose gel. Based on these results, it was calculated that phage from the 2.8×10⁷ plaques encode about 2×10⁷ different random amino acid sequences.

Example 4

(Panning for huPAR)

Peptides having an affinity for urokinase-type plasminogen activator receptor (uPAR) were identified as follows:

1.) 15mer phage (2.5×10¹⁰) prepared as described above were selected by coincubation with 10⁶ Sf9 cells expressing full length huPAR ("fluPAR", day 2 post infection) at room temperature for 60 minutes in Grace's medium with 2% nonfat milk. Binding phage were eluted with 6M urea (pH 2.2), the pH neutralized by adding 2M Tris-HCl, and assayed. The yield of binding phage was 0.0013% (3.3× $10^5$ pfu). The phage were amplified on solid agar plates as plaques, eluted with Tris-buffered saline, and precipitated with polyethylene glycol.

2.) The phage resulting from round 1 were reselected on COS cells transfected with fluPAR on day 2 post-infection, using $3.1×10^{11}$ phage on $2×10^5$ COS cells in DMEM with 2% nonfat milk and 10 mM HEPES. The phage were bound, eluted, assayed, and amplified as described in round 1. The yield of binding phage was 0.039% ($1.2×10^8$ pfu).

3.) The phage selected in round 2 were reselected on Sf9 cells expressing fluPAR (day 2 post-infection) as described for round 1 ($2.8×10^{10}$ phage on $10^6$ Sf9 cells). The yield of binding phage from this round was 5.40% ($1.5×10^9$ pfu), indicating a substantial enrichment in binding phage. Sample phage from the urea eluate were cloned, and their DNAs isolated and sequenced. Binding was assayed against Sf9 cells expressing fluPAR, and Sf9 cells expressing substance P receptor ("SPR," as a control). The results are as follows:

TABLE 1

Recovery of Phage using huPAR

| Sequence | Seq-ID | % Recovery huPAR | SPR | Specificity (uPAR/SPR) |
|---|---|---|---|---|
| AECLNGGTAVSNKYFSNIHWCN* | 37 | 6.8 | 0.008 | 857 |
| AESQTGTLNTLFWNTLR | 10 | 2.8 | 0.008 | 350 |
| AEWHPGLSFGSYLWSKT | 2 | 5.7 | 0.034 | 168 |
| AEMHRSLWEWYVPNQSA | 17 | 4.2 | 0.040 | 105 |
| AEPLDLWSLYSLPPLAM | 8 | 6.0 | 0.095 | 63 |
| AESSLWRIFSPSALMMS | 11 | 3.5 | 0.070 | 50 |
| AESSLWTRYAWPSMPSY | 4 | 12.1 | 0.260 | 47 |
| AEPALLNWSFFFNPGLH | 12 | 4.7 | 0.100 | 47 |
| AEPMPHSLNFSQYLWYT | 1 | 2.2 | 0.080 | 28 |
| AESLPTLTSILWGKESV | 9 | 0.5 | 0.022 | 24 |

*Positive control, residues 13-32 of the EGF-like domain of urokinase (not selected from library)

4.) The peptides encoded by 25 phage were then synthesized by solid phase peptide chemistry on an Applied Biosystems Model 430A peptide synthesizer, using Boc chemistry, or were obtained from Chiron Mimotopes, Ltd., as soluble peptides. All peptides contained the Ala-Glu dipeptide at the amino terminus and were amidated at the carboxy terminus.

Baculovirus-derived recombinant human urokinase receptor was expressed as a truncated, soluble molecule as described previously for mouse L-cells (Masucci et al., *J Biol Chem* (1991) 266:8655). The purified receptor was biotinylated with NHS-biotin, and immobilized at 1 µg/mL in PBS/0.1% BSA on streptavidin coated 96-well plates. Human uPA ATF (residues 1–135, obtained from M. Shuman, University of California, San Francisco) was iodinated using the Iodogen method (Pierce), and used as tracer. The $^{125}$I-ATF was incubated at 100–500 pM with increasing amounts of peptide from 1 nM to 10 µM in triplicate for 2 hours at room temperature in 0.1% BSA/PBS in a total volume of 200 µL. The plates were then washed 3 times with PBS/BSA, and the remaining bound radioactivity determined.

TABLE 2

Affinity of Synthesized Peptides

| Sequence | Seq ID | #clones | Yield % | Affinity (µM) |
|---|---|---|---|---|
| AEPMPHSLNFSQYLWYT | 1 | 11 | 2.2 | 0.015* |
| AEWHPGLSFGSYLWSKT | 2 | 7 | 5.7 | 0.35 |
| AEHTYSSLWDTYSPLAF | 3 | 8 |  | 0.35* |
| AESSLWTRYAWPSMPSY | 4 | 5 | 12.1 | 0.35 |
| AELDLWMRHYPLSFSNR | 5 | 1 |  | 0.8* |
| AEWSFYNLHLPEPQTIF | 6 | 3 |  | 5 |
| AETLFMDLWHDKHILLT | 7 | 5 |  | 7* |
| AEPLDLWSLYSLPPLAM | 8 | 2 | 6.0 | 5 |
| AESLPTLTSILWGKESV | 9 | 1 | 0.5 | 7 |
| AESQTGTLNTLFWNTLR | 10 | 10 | 2.8 | 7 |
| AESSLWRIFSPSALMMS | 11 | 1 | 3.5 | 7 |
| AEPALLNWSFFFNPGLH | 12 | 1 | 4.7 | 3 |
| AEAWFLSNTMKALSARL | 13 | 1 |  | 5 |
| AEPTLWQLYQFPLRLSG | 14 | 1 |  | 4* |
| AEISFSELMWLRSTPAF | 15 | 1 |  | 6* |
| AEWITSSPPLTQYLWGF | 16 | 1 |  | 10 |
| AEMHRSLWEWYVPNQSA | 17 | 9 | 4.2 | — |
| AEIKTDEKMGLWDLYSM | 18 | 1 |  | 25* |
| AEILNFPLWHEPLWSTE | 19 | 2 |  | 15* |
| AELSEADLWITWFGMGS | 20 | 1 |  | 20* |
| AESVQYSKLWKPNTTLA | 21 | 1 |  | >50 |
| AEPLSLYQKKTLRHFAN | 22 | 1 |  | >50 |
| AELPRTNPVTAVKNPSF | 23 | 1 |  | >50 |
| AEQLNRSIPDLQFSMFN | 24 | 1 |  | NA |
| AESHIKSLLDSSTWFLP | 25 | 1 |  | NA |

*Assay performed at 100 pM ATF, 0.3 µg/ml suPAR in 200 µL. Other assays are corrected to these conditions; corrections are about 3 × from previous assay conditions.

Example 5

(Formulation of huPA Antagonists)

huPA antagonist formulations suitable for use in chemotherapy are prepared as follows:

A) Injectable Formulation:

| AEPMPHSLNFSQYLWYT (SEQ ID NO: 1) | 25.0 mg |
|---|---|
| $Na_2HPO_4$ (0.5M) | 0.5 mL |
| mannitol (25%) | 2.5 mL |
| sodium laureate (1%) | 2.5 mL |
| pH | 7.5 |
| PBS qs | 20.0 mL |

This formulation is prepared following the procedure set forth in U.S. Pat. No. 4,816,440, incorporated herein by reference. The formulation is administered by parenteral injection at the site to be treated. The formulation is also generally suitable for administration as eyedrops directly to the conjunctiva, or by intranasal administration as an aerosol. Alternatively, a concentrated formulation (e.g., reducing the phosphate buffered saline to 2 mL) may be used to fill an Alzet® minipump, and the minipump implanted at the site to be treated.

B) Ophthalmic Preparation:

| AEPMPHSLNFSQYLWYT (SEQ ID NO: 1) | 1.0 mg |
|---|---|
| fibronectin | 69.0 mg |
| albumin | 37.5 mg |
| water qs | 3.0 mL |
| HCl (0.01M) qs | pH 4.0 |

This dosage form is prepared following the procedure set forth in U.S. Pat. No. 5,124,155, incorporated herein by reference. The fibronectin and albumin are dissolved in water to form a 3.0 mL solution, and HCl added to a pH of 4.0, causing the fibronectin to flocculate. The flocculent is filtered, and combined with the peptide. The mixture is then placed in a contact lens mold, and the mold closed for 30 min to form a corneal "shield" in the shape of a contact lens. The shield releases peptide over a period of time, and is useful for preventing angiogenesis of corneal tissue following ophthalmic surgery.

The present invention has been described with reference to specific embodiments. However, this application is intended to cover those changes and substitutions which may be made by those skilled in the art without departing from the spirit and the scope of the appended claims.

What is claimed:

1. An oligonucleotide which comprises a sequence encoding a peptide selected from the group consisting of
AEPMPHSLNFSQYLWYT (SEQ ID NO:1),
AEWHPGLSFGSYLWSKT (SEQ ID NO:2),
AEHTYSSLWDTYSPLAF (SEQ ID NO:3),
AESSLWTRYAWPSMPSY (SEQ ID NO:4),
AELDLWMRHYPLSFSNR (SEQ ID NO:5),
AEWSFYNLHLPEPQTIF (SEQ ID NO:6),
AEPLDLWSLYSLPPLAM (SEQ ID NO:8),
AEPALLNWSFFFNPGLH (SEQ ID NO:12),
AEAWFLSNTMKALSARL (SEQ ID NO:13),
AEPTLWQLYQFPLRLSG (SEQ ID NO:14), and
an active analog or active portion of said peptides thereof.

* * * * *

SEQUENCE LISTING ( 1 ) GENERAL INFORMATION:

( i i i ) NUMBER OF SEQUENCES: 37

( 2 ) INFORMATION FOR SEQ ID NO:1:

( i ) SEQUENCE CHARACTERISTICS:
        ( A ) LENGTH: 17 amino acids
        ( B ) TYPE: amino acid
        ( D ) TOPOLOGY: linear ( i i ) MOLECULE TYPE: peptide ( i i i ) HYPOTHETICAL: NO ( x i ) SEQUENCE DESCRIPTION: SEQ ID NO:1:

```
Ala  Glu  Pro  Met  Pro  His  Ser  Leu  Asn  Phe  Ser  Gln  Tyr  Leu  Trp  Tyr
1                  5                        10                            15
Thr
```

( 2 ) INFORMATION FOR SEQ ID NO:2:

( i ) SEQUENCE CHARACTERISTICS:
        ( A ) LENGTH: 17 amino acids
        ( B ) TYPE: amino acid
        ( D ) TOPOLOGY: linear ( i i ) MOLECULE TYPE: peptide ( i i i ) HYPOTHETICAL: NO ( x i ) SEQUENCE DESCRIPTION: SEQ ID NO:2:

```
Ala  Glu  Trp  His  Pro  Gly  Leu  Ser  Phe  Gly  Ser  Tyr  Leu  Trp  Ser  Lys
1                  5                        10                            15
Thr
```

( 2 ) INFORMATION FOR SEQ ID NO:3:

( i ) SEQUENCE CHARACTERISTICS:
        ( A ) LENGTH: 17 amino acids
        ( B ) TYPE: amino acid
        ( D ) TOPOLOGY: linear ( i i ) MOLECULE TYPE: peptide ( i i i ) HYPOTHETICAL: NO ( x i ) SEQUENCE DESCRIPTION: SEQ ID NO:3:

```
Ala  Glu  His  Thr  Tyr  Ser  Ser  Leu  Trp  Asp  Thr  Tyr  Ser  Pro  Leu  Ala
1                  5                        10                            15
Phe
```

( 2 ) INFORMATION FOR SEQ ID NO:4:

( i ) SEQUENCE CHARACTERISTICS:
        ( A ) LENGTH: 17 amino acids
        ( B ) TYPE: amino acid
        ( D ) TOPOLOGY: linear (i i) MOLECULE TYPE: peptide (i i i) HYPOTHETICAL: NO (x i) SEQUENCE DESCRIPTION: SEQ ID NO:4:

```
Ala  Glu  Ser  Ser  Leu  Trp  Thr  Arg  Tyr  Ala  Trp  Pro  Ser  Met  Pro  Ser
1                   5                        10                       15
Tyr
```

(2) INFORMATION FOR SEQ ID NO:5:

(i) SEQUENCE CHARACTERISTICS:
        (A) LENGTH: 17 amino acids
        (B) TYPE: amino acid
        (D) TOPOLOGY: linear (i i) MOLECULE TYPE: peptide (i i i) HYPOTHETICAL: NO (x i) SEQUENCE DESCRIPTION: SEQ ID NO:5:

```
Ala  Glu  Leu  Asp  Leu  Trp  Met  Arg  His  Tyr  Pro  Leu  Ser  Phe  Ser  Asn
1                   5                        10                       15
Arg
```

(2) INFORMATION FOR SEQ ID NO:6:

(i) SEQUENCE CHARACTERISTICS:
        (A) LENGTH: 17 amino acids
        (B) TYPE: amino acid
        (D) TOPOLOGY: linear (i i) MOLECULE TYPE: peptide (i i i) HYPOTHETICAL: NO (x i) SEQUENCE DESCRIPTION: SEQ ID NO:6:

```
Ala  Glu  Trp  Ser  Phe  Tyr  Asn  Leu  His  Leu  Pro  Glu  Pro  Gln  Thr  Ile
1                   5                        10                       15
Phe
```

(2) INFORMATION FOR SEQ ID NO:7:

(i) SEQUENCE CHARACTERISTICS:
        (A) LENGTH: 17 amino acids
        (B) TYPE: amino acid
        (D) TOPOLOGY: linear (i i) MOLECULE TYPE: peptide (i i i) HYPOTHETICAL: NO (x i) SEQUENCE DESCRIPTION: SEQ ID NO:7:

```
Ala  Glu  Thr  Leu  Phe  Met  Asp  Leu  Trp  His  Asp  Lys  His  Ile  Leu  Leu
1                   5                        10                       15
Thr
```

(2) INFORMATION FOR SEQ ID NO:8:

(i) SEQUENCE CHARACTERISTICS:
        (A) LENGTH: 17 amino acids
        (B) TYPE: amino acid
        (C) STRANDEDNESS: single
        (D) TOPOLOGY: linear (i i) MOLECULE TYPE: peptide (i i i) HYPOTHETICAL: NO (x i) SEQUENCE DESCRIPTION: SEQ ID NO:8:

```
Ala Glu Pro Leu Asp Leu Trp Ser Leu Tyr Ser Leu Pro Pro Leu Ala
1               5                   10                  15
Met
```

(2) INFORMATION FOR SEQ ID NO:9:

(i) SEQUENCE CHARACTERISTICS:
      (A) LENGTH: 17 amino acids
      (B) TYPE: amino acid
      (D) TOPOLOGY: linear (i i) MOLECULE TYPE: peptide (i i i) HYPOTHETICAL: NO (x i) SEQUENCE DESCRIPTION: SEQ ID NO:9:

```
Ala Glu Ser Leu Pro Thr Leu Thr Ser Ile Leu Trp Gly Lys Glu Ser
1               5                   10                  15
Val
```

(2) INFORMATION FOR SEQ ID NO:10:

(i) SEQUENCE CHARACTERISTICS:
      (A) LENGTH: 17 amino acids
      (B) TYPE: amino acid
      (D) TOPOLOGY: linear (i i) MOLECULE TYPE: peptide (i i i) HYPOTHETICAL: NO (x i) SEQUENCE DESCRIPTION: SEQ ID NO:10:

```
Ala Glu Ser Gln Thr Gly Thr Leu Asn Thr Leu Phe Trp Asn Thr Leu
1               5                   10                  15
Arg
```

(2) INFORMATION FOR SEQ ID NO:11:

(i) SEQUENCE CHARACTERISTICS:
      (A) LENGTH: 17 amino acids
      (B) TYPE: amino acid
      (D) TOPOLOGY: linear (i i) MOLECULE TYPE: peptide (i i i) HYPOTHETICAL: NO (x i) SEQUENCE DESCRIPTION: SEQ ID NO:11:

```
Ala Glu Ser Ser Leu Trp Arg Ile Phe Ser Pro Ser Ala Leu Met Met
1               5                   10                  15
Ser
```

(2) INFORMATION FOR SEQ ID NO:12:

(i) SEQUENCE CHARACTERISTICS:
      (A) LENGTH: 17 amino acids
      (B) TYPE: amino acid
      (D) TOPOLOGY: linear (i i) MOLECULE TYPE: peptide (i i i) HYPOTHETICAL: NO (x i) SEQUENCE DESCRIPTION: SEQ ID NO:12:

```
Ala Glu Pro Ala Leu Leu Asn Trp Ser Phe Phe Phe Asn Pro Gly Leu
1               5                   10                      15

His
```

( 2 ) INFORMATION FOR SEQ ID NO:13:

( i ) SEQUENCE CHARACTERISTICS:
        ( A ) LENGTH: 17 amino acids
        ( B ) TYPE: amino acid
        ( D ) TOPOLOGY: linear ( i i ) MOLECULE TYPE: peptide ( i i i ) HYPOTHETICAL: NO ( x i ) SEQUENCE DESCRIPTION: SEQ ID NO:13:

```
Ala Glu Ala Trp Phe Leu Ser Asn Thr Met Lys Ala Leu Ser Ala Arg
1               5                   10                      15

Leu
```

( 2 ) INFORMATION FOR SEQ ID NO:14:

( i ) SEQUENCE CHARACTERISTICS:
        ( A ) LENGTH: 17 amino acids
        ( B ) TYPE: amino acid
        ( D ) TOPOLOGY: linear ( i i ) MOLECULE TYPE: peptide ( i i i ) HYPOTHETICAL: NO ( x i ) SEQUENCE DESCRIPTION: SEQ ID NO:14:

```
Ala Glu Pro Thr Leu Trp Gln Leu Tyr Gln Phe Pro Leu Arg Leu Ser
1               5                   10                      15

Gly
```

( 2 ) INFORMATION FOR SEQ ID NO:15:

( i ) SEQUENCE CHARACTERISTICS:
        ( A ) LENGTH: 17 amino acids
        ( B ) TYPE: amino acid
        ( D ) TOPOLOGY: linear ( i i ) MOLECULE TYPE: peptide ( i i i ) HYPOTHETICAL: NO ( x i ) SEQUENCE DESCRIPTION: SEQ ID NO:15:

```
Ala Glu Ile Ser Phe Ser Glu Leu Met Trp Leu Arg Ser Thr Pro Ala
1               5                   10                      15

Phe
```

( 2 ) INFORMATION FOR SEQ ID NO:16:

( i ) SEQUENCE CHARACTERISTICS:
        ( A ) LENGTH: 17 amino acids
        ( B ) TYPE: amino acid
        ( D ) TOPOLOGY: linear ( i i ) MOLECULE TYPE: peptide ( i i i ) HYPOTHETICAL: NO ( x i ) SEQUENCE DESCRIPTION: SEQ ID NO:16:

```
Ala Glu Trp Ile Thr Ser Ser Pro Pro Leu Thr Gln Tyr Leu Trp Gly
1               5                   10                      15

Phe
```

( 2 ) INFORMATION FOR SEQ ID NO:17:

( i ) SEQUENCE CHARACTERISTICS:
      ( A ) LENGTH: 17 amino acids
      ( B ) TYPE: amino acid
      ( D ) TOPOLOGY: linear ( i i ) MOLECULE TYPE: peptide ( i i i ) HYPOTHETICAL: NO ( x i ) SEQUENCE DESCRIPTION: SEQ ID NO:17:

```
Ala Glu Met His Arg Ser Leu Trp Glu Trp Tyr Val Pro Asn Gln Ser
1               5                   10                  15
Ala
```

( 2 ) INFORMATION FOR SEQ ID NO:18:

( i ) SEQUENCE CHARACTERISTICS:
      ( A ) LENGTH: 17 amino acids
      ( B ) TYPE: amino acid
      ( D ) TOPOLOGY: linear ( i i ) MOLECULE TYPE: peptide ( i i i ) HYPOTHETICAL: NO ( x i ) SEQUENCE DESCRIPTION: SEQ ID NO:18:

```
Ala Glu Ile Lys Thr Asp Glu Lys Met Gly Leu Trp Asp Leu Tyr Ser
1               5                   10                  15
Met
```

( 2 ) INFORMATION FOR SEQ ID NO:19:

( i ) SEQUENCE CHARACTERISTICS:
      ( A ) LENGTH: 17 amino acids
      ( B ) TYPE: amino acid
      ( D ) TOPOLOGY: linear ( i i ) MOLECULE TYPE: peptide ( i i i ) HYPOTHETICAL: NO ( x i ) SEQUENCE DESCRIPTION: SEQ ID NO:19:

```
Ala Glu Ile Leu Asn Phe Pro Leu Trp His Glu Pro Leu Trp Ser Thr
1               5                   10                  15
Glu
```

( 2 ) INFORMATION FOR SEQ ID NO:20:

( i ) SEQUENCE CHARACTERISTICS:
      ( A ) LENGTH: 17 amino acids
      ( B ) TYPE: amino acid
      ( D ) TOPOLOGY: linear ( i i ) MOLECULE TYPE: peptide ( i i i ) HYPOTHETICAL: NO ( x i ) SEQUENCE DESCRIPTION: SEQ ID NO:20:

```
Ala Glu Leu Ser Glu Ala Asp Leu Trp Ile Thr Trp Phe Gly Met Gly
1               5                   10                  15
Ser
```

( 2 ) INFORMATION FOR SEQ ID NO:21:

( i ) SEQUENCE CHARACTERISTICS:
    ( A ) LENGTH: 17 amino acids
    ( B ) TYPE: amino acid
    ( D ) TOPOLOGY: linear ( i i ) MOLECULE TYPE: peptide ( i i i ) HYPOTHETICAL: NO ( x i ) SEQUENCE DESCRIPTION: SEQ ID NO:21:

```
Ala  Glu  Ser  Val  Gln  Tyr  Ser  Lys  Leu  Trp  Lys  Pro  Asn  Thr  Thr  Leu
1                   5                        10                       15

Ala
```

( 2 ) INFORMATION FOR SEQ ID NO:22:

( i ) SEQUENCE CHARACTERISTICS:
    ( A ) LENGTH: 17 amino acids
    ( B ) TYPE: amino acid
    ( D ) TOPOLOGY: linear ( i i ) MOLECULE TYPE: peptide ( i i i ) HYPOTHETICAL: NO ( x i ) SEQUENCE DESCRIPTION: SEQ ID NO:22:

```
Ala  Glu  Pro  Leu  Ser  Leu  Tyr  Gln  Lys  Lys  Thr  Leu  Arg  His  Phe  Ala
1                   5                        10                       15

Asn
```

( 2 ) INFORMATION FOR SEQ ID NO:23:

( i ) SEQUENCE CHARACTERISTICS:
    ( A ) LENGTH: 17 amino acids
    ( B ) TYPE: amino acid
    ( D ) TOPOLOGY: linear ( i i ) MOLECULE TYPE: peptide ( i i i ) HYPOTHETICAL: NO ( x i ) SEQUENCE DESCRIPTION: SEQ ID NO:23:

```
Ala  Glu  Leu  Pro  Arg  Thr  Asn  Pro  Val  Thr  Ala  Val  Lys  Asn  Pro  Ser
1                   5                        10                       15

Phe
```

( 2 ) INFORMATION FOR SEQ ID NO:24:

( i ) SEQUENCE CHARACTERISTICS:
    ( A ) LENGTH: 17 amino acids
    ( B ) TYPE: amino acid
    ( D ) TOPOLOGY: linear ( i i ) MOLECULE TYPE: peptide ( i i i ) HYPOTHETICAL: NO ( x i ) SEQUENCE DESCRIPTION: SEQ ID NO:24:

```
Ala  Glu  Gln  Leu  Asn  Arg  Ser  Ile  Pro  Asp  Leu  Gln  Phe  Ser  Met  Phe
1                   5                        10                       15

Asn
```

( 2 ) INFORMATION FOR SEQ ID NO:25:

( i ) SEQUENCE CHARACTERISTICS:
    ( A ) LENGTH: 17 amino acids
    ( B ) TYPE: amino acid
    ( D ) TOPOLOGY: linear (i i) MOLECULE TYPE: peptide (i i i) HYPOTHETICAL: NO (x i) SEQUENCE DESCRIPTION: SEQ ID NO:25:

```
Ala Glu Ser His Ile Lys Ser Leu Leu Asp Ser Ser Thr Trp Phe Leu
1               5                   10                  15
Pro
```

(2) INFORMATION FOR SEQ ID NO:26:

(i) SEQUENCE CHARACTERISTICS:
  (A) LENGTH: 85 base pairs
  (B) TYPE: nucleic acid
  (C) STRANDEDNESS: single
  (D) TOPOLOGY: linear (i i) MOLECULE TYPE: cDNA (i i i) HYPOTHETICAL: NO (x i) SEQUENCE DESCRIPTION: SEQ ID NO:26:

```
CTTTCTATTC TCACTCCGCT GAANNSNNSN NSNNSNNSNN SNNSNNSNNS NNSNNSNNSN    60
NSNNSNNSCC GCCTCCACCT CCACC                                         85
```

(2) INFORMATION FOR SEQ ID NO:27:

(i) SEQUENCE CHARACTERISTICS:
  (A) LENGTH: 93 base pairs
  (B) TYPE: nucleic acid
  (C) STRANDEDNESS: single
  (D) TOPOLOGY: linear (i i) MOLECULE TYPE: cDNA (i i i) HYPOTHETICAL: NO (i x) FEATURE:
  (A) NAME/KEY: misc_feature
  (B) LOCATION: 22..66
  (C) IDENTIFICATION METHOD: experimental
  (D) OTHER INFORMATION: /function="Random hybridization"
   / evidence=EXPERIMENTAL
   / standard_name="inosine"
   / label=inosine (x i) SEQUENCE DESCRIPTION: SEQ ID NO:27:

```
GGCCGGTGGA GGTGGAGGCG GNNNNNNNNN NNNNNNNNNN NNNNNNNNNN NNNNNNNNNN    60
NNNNNNTTCA GCGGAGTGAG AATAGAAAGG TAC                                 93
```

(2) INFORMATION FOR SEQ ID NO:28:

(i) SEQUENCE CHARACTERISTICS:
  (A) LENGTH: 23 amino acids
  (B) TYPE: amino acid
  (D) TOPOLOGY: linear (i i) MOLECULE TYPE: peptide (i i i) HYPOTHETICAL: NO (i x) FEATURE:
  (A) NAME/KEY: Region
  (B) LOCATION: 3..17
  (D) OTHER INFORMATION: /label=randomer
   / note="Random amino acid sequence"

(x i) SEQUENCE DESCRIPTION: SEQ ID NO:28:

```
Ala Glu Xaa Xaa Xaa Xaa Xaa Xaa Xaa Xaa Xaa Xaa Xaa Xaa Xaa Xaa
```

```
         1               5                  10                 15
     Xaa Pro Pro Pro Pro Pro Pro
                    20
```

(2) INFORMATION FOR SEQ ID NO:29:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (xi) SEQUENCE DESCRIPTION: SEQ ID NO:29:

GCTGCCCGAG AGATCTGTAT ATATGAGTAA ACTTGG       36

(2) INFORMATION FOR SEQ ID NO:30:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (xi) SEQUENCE DESCRIPTION: SEQ ID NO:30:

GCAGGCTCGG GAATTCGGGA AATGTGCGCG GAACCC       36

(2) INFORMATION FOR SEQ ID NO:31:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (xi) SEQUENCE DESCRIPTION: SEQ ID NO:31:

AAACTTCCTC ATGAAAAAGT C       21

(2) INFORMATION FOR SEQ ID NO:32:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (xi) SEQUENCE DESCRIPTION: SEQ ID NO:32:

AGAATAGAAA GGTACCACTA AAGGA       25

(2) INFORMATION FOR SEQ ID NO:33:

(i) SEQUENCE CHARACTERISTICS:
        (A) LENGTH: 39 base pairs
        (B) TYPE: nucleic acid
        (C) STRANDEDNESS: single -continued (D) TOPOLOGY: linear (ii) MOLECULE TYPE: cDNA (iii) HYPOTHETICAL: NO (xi) SEQUENCE DESCRIPTION: SEQ ID NO:33:

TTTAGTGGTA CCTTTCTATT CTCACTCGGC CGAAACTGT            39

(2) INFORMATION FOR SEQ ID NO:34:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (xi) SEQUENCE DESCRIPTION: SEQ ID NO:34:

AAAGCGCAGT CTCTGAATTT ACCG                            24

(2) INFORMATION FOR SEQ ID NO:35:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (xi) SEQUENCE DESCRIPTION: SEQ ID NO:35:

TCGAAAGCAA GCTGATAAAC CG                              22

(2) INFORMATION FOR SEQ ID NO:36:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (xi) SEQUENCE DESCRIPTION: SEQ ID NO:36:

ACAGACAGCC CTCATAGTTA GCG                             23

(2) INFORMATION FOR SEQ ID NO:37:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (iii) HYPOTHETICAL: NO (v) FRAGMENT TYPE: N-terminal (xi) SEQUENCE DESCRIPTION: SEQ ID NO:37:

| | | | | | | | | | | | | | | | |
|---|---|---|---|---|---|---|---|---|---|---|---|---|---|---|---|
| Ala | Glu | Cys | Leu | Asn | Gly | Gly | Thr | Ala | Val | Ser | Asn | Lys | Tyr | Phe | Ser |
| 1 | | | | 5 | | | | | 10 | | | | | 15 | |
| Asn | Ile | His | Trp | Cys | Asn | | | | | | | | | | |
| | | | 20 | | | | | | | | | | | | |